(12) United States Patent (10) Patent No.: US 8,290,226 B2
Gühring et al. (45) Date of Patent: Oct. 16, 2012

(54) METHOD FOR DETERMINING AND DISPLAYING AT LEAST ONE PIECE OF INFORMATION ON A TARGET VOLUME

(75) Inventors: Jens Gühring, Monmouth Junction, NJ (US); Michaela Schmidt, Buckenhof (DE)

(73) Assignee: Siemens Aktiengesellschaft, Munich (DE)

( * ) Notice: Subject to any disclaimer, the term of this patent is extended or adjusted under 35 U.S.C. 154(b) by 687 days.

(21) Appl. No.: 12/226,858

(22) PCT Filed: Apr. 24, 2007

(86) PCT No.: PCT/EP2007/053996
§ 371 (c)(1),
(2), (4) Date: Nov. 13, 2008

(87) PCT Pub. No.: WO2007/128686
PCT Pub. Date: Nov. 15, 2007

(65) Prior Publication Data
US 2009/0220050 A1 Sep. 3, 2009

(30) Foreign Application Priority Data
May 4, 2006 (DE) .......................... 10 2006 020 864

(51) Int. Cl.
*G06K 9/00* (2006.01)
(52) U.S. Cl. ........ 382/128; 382/129; 382/130; 382/131; 382/132; 382/133; 382/168; 382/171; 382/181; 382/201; 382/202; 382/203; 600/407; 600/427; 600/436; 128/922
(58) Field of Classification Search .................. 382/128, 382/129, 130, 131, 132, 133, 168, 171, 181, 382/21, 201–203, 219, 232, 254, 255, 256, 382/257–258, 274, 276–277, 282, 286–294; 600/407, 427, 436; 378/4–27; 128/922
See application file for complete search history.

(56) References Cited

U.S. PATENT DOCUMENTS
5,782,762 A * 7/1998 Vining .......................... 600/407
(Continued)

FOREIGN PATENT DOCUMENTS
CN 1682657 A 10/2005
(Continued)

OTHER PUBLICATIONS
Positano V. et al: Automatic Characterization of Myocardial Perfusion in Contrast Enhanced MRI, EURASIP Journal on Applied Signal Processing Hindawi USA, Bd. 2003, Nr. 5, Jan. 4, 2003, pp. 413-421, XP002496466, ISSN: 1110-8657.
(Continued)

*Primary Examiner* — Georgia Y Epps
*Assistant Examiner* — Sultan Chowdhury
(74) *Attorney, Agent, or Firm* — Harness, Dickey & Pierce, P.L.C.

(57) ABSTRACT

Disclosed is a method for determining and displaying at least one piece of information on a target volume, especially in a human body, the information being obtained from an image record. At least one embodiment of the method includes: a first and at least one second image record of a target zone encompassing the target volume are recorded, the first image record having a higher contrast regarding the boundaries of the target volume, and the first and the second image record being registered together; the target volume is segmented in the first image record; target volume image data.

22 Claims, 3 Drawing Sheets

U.S. PATENT DOCUMENTS

| | | | |
|---|---|---|---|
| 5,875,108 A * | 2/1999 | Hoffberg et al. | 700/17 |
| 6,701,174 B1 * | 3/2004 | Krause et al. | 600/407 |
| 7,106,892 B2 | 9/2006 | Breeuwer et al. | |
| 7,388,973 B2 * | 6/2008 | Fidrich et al. | 382/128 |
| 7,444,011 B2 * | 10/2008 | Pan et al. | 382/131 |
| 7,460,699 B2 * | 12/2008 | O'Donnell et al. | 382/128 |
| 7,477,763 B2 * | 1/2009 | Willis et al. | 382/128 |
| 7,539,332 B1 * | 5/2009 | Al-Dayeh et al. | 382/128 |
| 7,876,938 B2 * | 1/2011 | Huang et al. | 382/128 |
| 2003/0208116 A1 | 11/2003 | Liang et al. | |
| 2004/0015072 A1 * | 1/2004 | Pelletier et al. | 600/410 |
| 2005/0065421 A1 * | 3/2005 | Burckhardt | 600/407 |
| 2005/0101855 A1 * | 5/2005 | Miga et al. | 600/407 |
| 2005/0135707 A1 | 6/2005 | Turek et al. | |
| 2005/0196027 A1 | 9/2005 | O'Donnell et al. | |
| 2006/0013459 A1 | 1/2006 | Katscher et al. | |
| 2006/0173268 A1 * | 8/2006 | Mullick et al. | 600/407 |
| 2007/0127789 A1 * | 6/2007 | Hoppel et al. | 382/128 |
| 2009/0074264 A1 * | 3/2009 | Pekar et al. | 382/128 |

FOREIGN PATENT DOCUMENTS

| | | |
|---|---|---|
| DE | 10214254 A1 | 10/2003 |
| DE | 102004061435 A1 | 7/2005 |
| JP | 2006-50009 | 1/2006 |

OTHER PUBLICATIONS

Santos A. et al: Multimodality image integration for radiotherapy treatment, an easy approach, Proceedings of the Spie—The International Society for Optical Engineering Spie-Int. Soc. Opt. Eng USA, Bd. 4319, 2001, pp. 715-723, XP002496465, ISSN: 0277-786X.

Notification of Reasons for Refusal dated May 8, 2012, issued in Patent Application No. 2009-508313.

* cited by examiner

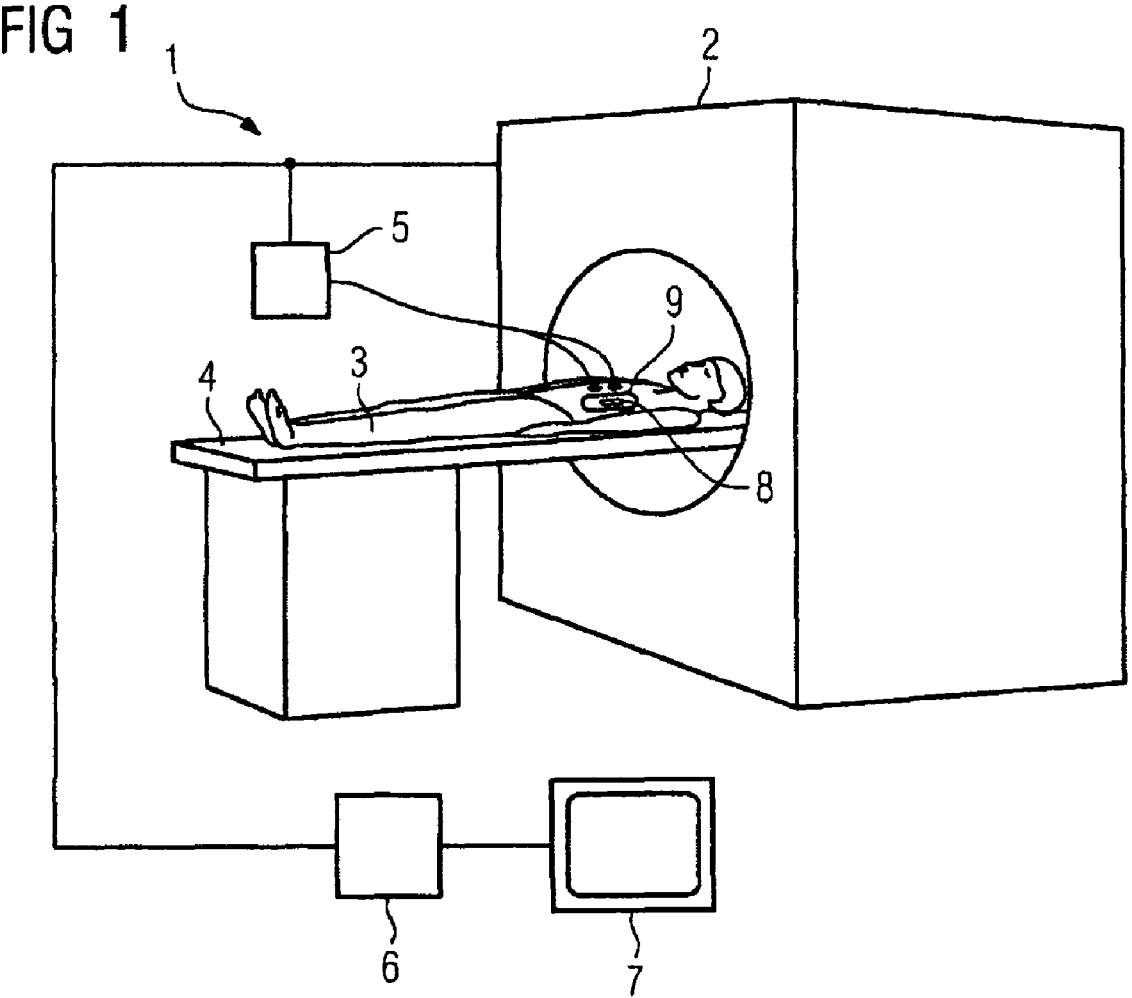

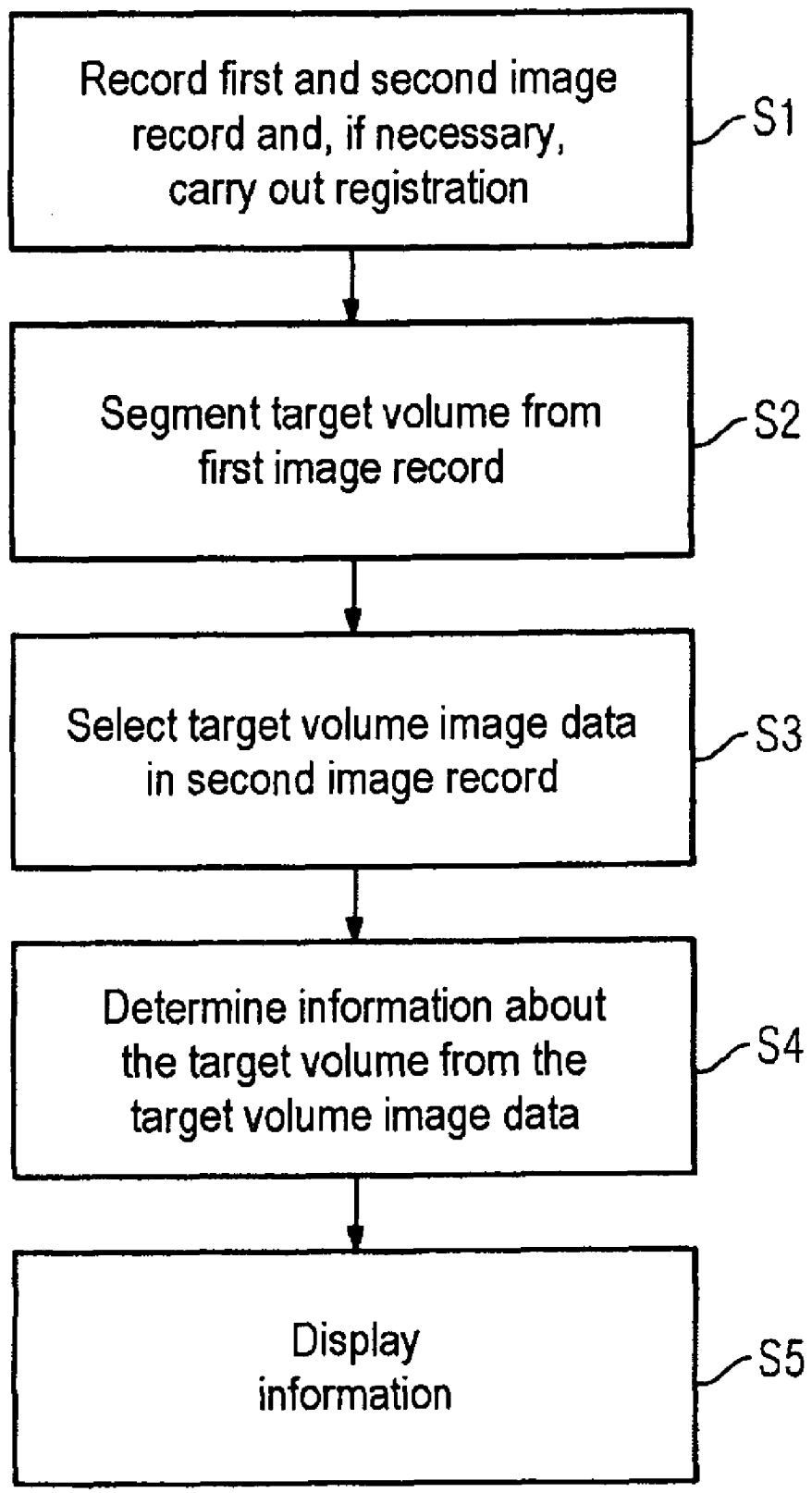

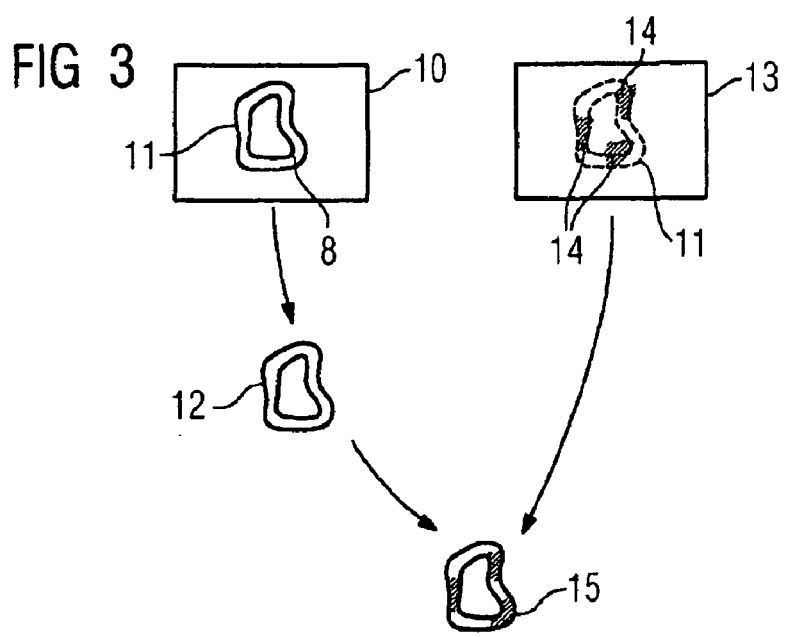
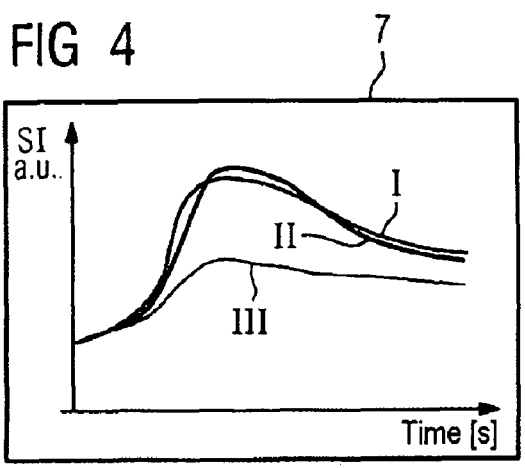
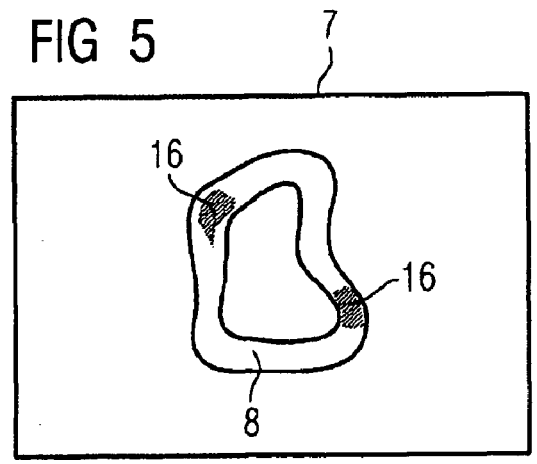
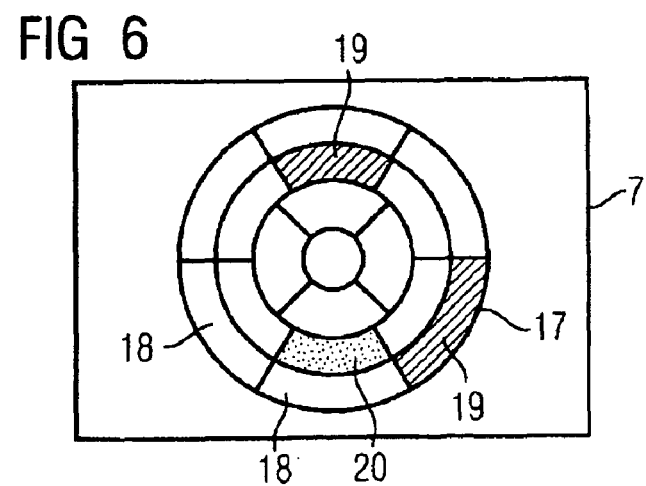

METHOD FOR DETERMINING AND DISPLAYING AT LEAST ONE PIECE OF INFORMATION ON A TARGET VOLUME

PRIORITY STATEMENT

This application is the national phase under 35 U.S.C. §371 of PCT International Application No. PCT/EP2007/053996 which has an International filing date of Apr. 24, 2007, which designated the United States of America and which claims priority on German application No. 10 2006 020 864.1 filed May 4, 2006, the entire contents of which are hereby incorporated herein by reference.

FIELD

At least one embodiment of the invention generally relates to a method for determining and displaying at least one item of information about a target volume, in at least one particular embodiment in the human body, with the information being obtained from an image record, and the invention also relates to a medical examination apparatus.

BACKGROUND

In the field of medicine, many image recording techniques are known in which image records are recorded, taking into account different parameters so that a particular item of information about a target volume can be determined therefrom and can be displayed.

One example of this is magnetic resonance perfusion records, with the aid of which the perfusion of a particular tissue region, for example, is intended to be measured. In the process, a contrast agent is injected and, for example, observations are made regarding the speed at which this contrast agent moves into the tissue and out of the tissue. Since the contrast agent is transported by the blood, a statement regarding the perfusion is possible. Such perfusion image records are often recorded once at rest and once under stress, whereupon the results of the two records are compared. Defects can easily be recognized by comparing these records.

Another known example of such records is so-called viability records. Here, the fact that the contrast agent accumulates in dead tissue is used so that diseased tissue can be distinguished from healthy tissue. This in turn is of interest to various target volumes, in particular tissue regions.

In order to be able to obtain the desired information from such image records, parameters are used which clearly highlight the peculiarities of the target volume (and the surroundings of the target volume) which contain this information; this often occurs to the detriment of the contrast or the resolution of natural anatomical features. By way of example, the perfusion and viability records are recorded such that the contrast agent wash-in and later accumulation can be recognized particularly well in the images obtained.

However, in this, case it important to observe only the target volume which is actually of interest. For example, if the target volume is the myocardium, with ischemic or necrotic tissue intended to be found, then only data from the myocardium can be taken into account for determining the information. For this reason, it is normal practice to segment the target volume in the records; this usually has to be carried out manually due to the lack of contrast of the anatomical boundaries, and is very error-prone. This in turn can lead to critical false information which incorrectly describes the state of health of a patient.

It is often the case that, within the scope of more extensive or precise examinations, a plurality of image records of a target volume or neighboring target volumes are actually recorded. By way of example, if the heart of a patient is intended to be examined for ischemia, both so-called function image records and perfusion or viability records are to be recorded in a magnetic resonance examination. The target volume must subsequently be segmented in each of these image records, requiring great effort.

SUMMARY

At least one embodiment of the invention develops a method so that more precise localization of the target volume in the image record is made possible and thus the reliability and quality of the information is increased.

In at least one embodiment, the following steps are provided in a method for determining and displaying at least one item of information about a target volume, in particular in the human body, with the information being obtained from an image record:
  recording a first and at least one second image record of a target area comprising the target volume, the first image record having a higher contrast with respect to the boundaries of the target volume, and the first and the second image record being registered to one another,
  segmenting the target volume in the first image record,
  selecting target volume image data in the second image record taking into account the segmentation and the registration,
  determining the information from the target volume image data, and displaying the information.

At least one embodiment of the invention advantageously uses the fact that a first image record with a higher contrast with respect to the boundary of the target volume is available which, for example, was recorded for determining a different item of information and in which the target volume can easily be segmented, or had to be segmented in any case, so that the segmentation is already present. In this case, it is particularly advantageous if the two image records were recorded with the same imaging apparatus, in particular even in the course of a single examination. Having previously been normal practice to separately segment all recorded image records with regard to the target volume, according to the invention, the segmentation of the contrast-rich image record, that is to say the most reliable segmentation, is now transferred to the other image records, in particular during post-processing. In the case of the same imaging apparatus, or in the case of imaging using two modalities which belong to one examination apparatus and have a fixed spatial relationship, it is usual for the registration between the first and the second image record to be known in principle in any case, due to the known geometric conditions and settings, which means that the image records are registered to one another in advance, possibly after a calibration. If the first and the second or the number of second image records are not yet registered to one another, registration can be carried out using a normal practice registration method.

Once the image records are registered to one another, it is possible to segment the target volume in one image record, namely in the first image record which should have the greatest contrast with respect to the boundary of the target volume. Of course, it is possible to segment the target volume prior to registration or even prior to recording the second image records. However, if the position, extent and orientation of the target volume are known in a single image record of the image records registered to one another, it is possible to likewise directly locate the image data of the other image records lying in the target volume. Hence, target volume image data in the second image record is selected, taking into account the segmentation and the registration, without segmenting the second image record. The information is now established from this target volume image data, the position of which is determined very precisely due to the high contrast of the first image record, and is displayed.

With the aid of the method according to at least one embodiment of the invention, the image records are thus not only evaluated more reliably, but this evaluation is additionally sped up and simplified due to segmentation being required only once since the highest contrast image record is selected.

Within the scope of at least one embodiment of the invention, it is possible to observe both three-dimensional image records and image records with two-dimensional records.

In the process, segmentation can be carried out automatically, semi-automatically or manually. The region growing algorithm is particularly suitable for automatic or semi-automatic segmentation. In the semi-automatic case, the user defines a starting point, or a number of starting points, around which the target volume is segmented. However, it is also possible to find these starting points in a fully automated fashion. In the case of manual or semi-automatic segmentation, an image representation of the first image record is advantageously displayed on a monitor or the like, on which a user can place his markings.

In this case, automatic segmentation is particularly advantageous. If the information is also established automatically, the user receives a display of the information desired by him after completing the recordings without the need for further action on his part. Laborious generation of markers or other inputs is dispensed with, but reliable information is nevertheless obtained due to the reference to the contrast-rich first image record.

In the field of medicine, regions subject to rhythmic motion due to respiration or heart beats are often intended to be recorded. Expediently, both or all image records are recorded in a respiration-triggered fashion so that the results of the segmentation can be transferred to the second image record without any problems. By way of example, a patient here can be asked to hold his breath. However, other methods of respiration triggering are also feasible.

The cardiac cycle is very much faster than the respiratory cycle. Usually, the cardiac cycle is measured by a suitable EKG machine. Using such an EKG machine, it is possible for both the first and the second image record to be recorded during the same EKG phase by means of EKG triggering. This shows comparison and transfer of the results between the image records. However, the first image record is in any case often recorded over an entire EKG cycle. In this case, it is possible for the images to be stored together with their EKG phase.

If the second image record is subsequently recorded in an EKG-triggered fashion, images having the same EKG phase in the first image record can be used for registration and segmentation. Of course, it is also possible for both the first and second image records to be recorded over an entire cycle. Subsets of the image records, recorded during the same cardiac phase, are then each related to one another. Finally, it is possible to record the second image record at fewer times during the EKG cycle.

It is of course possible, when records of a target region are moving rhythmically with the cardiac and/or respiratory cycle, for there to be no images of the first image record which exactly correspond to the EKG and/or respiratory phase of the second image record. In that case, it is expediently possible to establish a correction of the registration and/or segmentation on the basis of the deviating phase. In particular, in the process, it is possible to correspondingly interpolate the data associated with the two closest EKG phases when images of the first image record are recorded over an entire EKG cycle or respiratory cycle. However, other methods for establishing the correction are also feasible.

A different contrast with respect to the boundaries of the target volume can occur particularly when the first and/or the second image record are/is recorded after administering a contrast agent. In that case, the parameters of the imaging modality are adapted in such a way that the contrast agent can be recognized in the best possible manner, which could be to the detriment of other anatomical features. It is possible that it is then more difficult to recognize the latter. However, it is of course also possible that the contrast agent was administered for the first image record so that the target volume can be recognized more easily. Certain target volumes can only be made clearly visible after administering such a contrast agent and hence be made easy to segment.

The image records can be recorded using a magnetic resonance imaging scanner, in particular using the same magnetic resonance imaging scanner, with a different recording sequence being used in each case for the two image records. It is often the case that, during an examination, image records are recorded using different recording sequences, with different information being intended to be obtained therefrom. However, different recording sequences, with another such recording sequence being matched to a contrast agent for example, lead to different contrasts and resolutions. The method according to the invention makes an allowance for this by only selecting the image for segmenting which has the highest contrast with regard to the boundaries of the target volume, with the results of the segmentation then being transferred to the other image records.

In the case of cardiac examinations, suitable first image records having a high contrast of anatomical features are for example function image records or whole heart image records recorded by the magnetic resonance imaging scanners. Second image records can be for example the previously mentioned perfusion or viability image records. In order to obtain those records, a contrast agent is administered in each case. However, it is also possible to record both perfusion image records and viability image records after administering a contrast agent. In this case, perfusion data records are recorded shortly after administering the contrast agent (so-called first pass records), while the viability data records are recorded later, during which time the contrast agent can accumulate in the necrotic tissue.

The target volume can be the myocardium for this type of image records, to be precise for the function, whole heart, perfusion and viability image records. It is then possible to obtain information regarding perfusion or necrosis. Myocardium viability records are undertaken in particular after an ischemic event, with it being possible that, particularly after a myocardial infarct, wall motion defects, which are usually regional, occur as a result of avital myocardium cells (myocytes) or as a result of vital, but currently non-contracting, myocardial tissue.

As mentioned previously, it is possible, within the scope of embodiments of the invention, for more than one second image record to be recorded and that information from each second image record can be determined and displayed. The perfusion and viability image records, which have already been mentioned above, are an example of this. While the perfusion image records provide information about the perfusion and in the process provide information about ischemic (that is to say badly or not at all perfused) tissue areas, the viability data records provide statements about the presence of vital or avital tissue, or even completely necrotic regions.

Within the scope of the method according to at least one embodiment of the invention, the first image record need not just be used to segment the target volume. It is also possible to establish and display additional information about the target volume from the first image record. By way of example, a function image record is normally used to determine information about the cardiac output. The diastolic and systolic volumes can be determined, and the stroke volume or the so-called ejection fraction can be determined from this.

Expediently, it may also be possible not only to display the established information but also to image the first and/or the second image record and/or of parts of the first and/or the second image record. For example, further information can then be obtained, by observation, from these images.

In a particularly advantageous refinement, the information can be established in a location-dependent manner and the location-dependent information of an image representation of the first and/or the second image record can be displayed in a superposed fashion. By way of example, in the case of a viability record, imaging the heart can show which regions are necrotic, and where they are. The percentage of determined avital cells can for example be displayed in a representation, color-coded according to determined percentage ranges.

Furthermore, at least one embodiment of the invention relates to a medical examination apparatus, comprising an imaging apparatus, in particular a magnetic resonance imaging scanner, and a computer designed to carry out the method according to at least one embodiment of the invention.

BRIEF DESCRIPTION OF THE DRAWINGS

Further advantages and details of the present invention emerge from the example embodiments described in the following text, and from the drawings, in which:

FIG. 1 shows a medical examination apparatus according to an embodiment of the invention, FIG. 2 shows a flowchart of the method according to an embodiment of the invention, FIG. 3 shows a basic outline for explaining the method, FIG. 4 shows a possible display of information regarding the perfusion in a myocardium, FIG. 5 shows the illustration of perfusion information in an image representation of the first image record, and FIG. 6 shows an illustration of viability information in a so-called bull's eye plot.

DETAILED DESCRIPTION OF THE EXAMPLE EMBODIMENTS

FIG. 1 shows a medical examination apparatus 1 according to an embodiment of the invention. A magnetic resonance imaging scanner 2 is provided as imaging apparatus. A patient 3 is introduced into it on a patient couch 4. Furthermore, the patient 3 is connected to an EKG machine 5 so that the respective cardiac phase can be measured. The operation of the medical examination apparatus is controlled by a computer 6, which is connected to a monitor 7. A target volume 8 within a target region 9 inside the patient 3 is intended to be examined. The computer 6 is designed to carry out the method according to an embodiment of the invention.

In the following example embodiment of the method, it is intended that, by way of example, a cardiac examination of the patient 3 will be described. In this case, it is normal practice to record a plurality of types of magnetic resonance image records. Firstly, a so-called function image record is recorded as a first image record, which shows the anatomical contours particularly clearly and from which conclusions are intended to be drawn about the different functional properties of the heart. To this end, the end-diastolic and systolic volumes are determined and, if appropriate, optional further information is determined, for example the ejection fraction or the stroke volume. Furthermore, it is easy to recognize in the function image record the myocardium which forms the actual target volume because, for example, infarct scars are intended to be sought.

Statements regarding infarct scars, that is to say ischemic tissue or even necrotic tissue, or avital myocytes can be established from perfusion image records and/or viability data records. These second image records are recorded once a contrast agent is administered. In the process, the magnetic resonance imaging scanner 2 is actuated by the computer 6 with a different measurement sequence which particularly highlights the contrast agent. Other anatomical properties are therefore not highlighted to the same extent. Previously, it was normal practice to now segment the myocardium in the second image records using a laborious manual process.

Although embodiments of the invention are not limited to a single second image record, perfusion image records as second image records will discussed here in greater detail.

FIG. 2 shows a flowchart of the method according to an embodiment of the invention. The image records are first of all recorded in step S1. In the discussed example of the cardiac examination with the aid of function image records and perfusion image records, these can, be recorded in a different sequence. It is normal practice to record images both in stress conditions and in rest conditions. Only severe perfusion disorders can be detected in rest conditions; however, in stress conditions it is also possible to unmask further, less severe perfusion disorders. A contrast agent is firstly administered intravenously to the patient 3. Thereafter, recording of the rest perfusion image record commences immediately. A technique for holding the breath was previously practiced with the patient 3, so that the patient 3 is able to remain in a particular respiratory phase for approximately 25 to 30 seconds. Using today's measurement sequences, it is possible to record, for example, in each case four slices in the target region 9 of the patient 3 per cardiac cycle over a corresponding period of time.

Recording each of these four slices is EKG-triggered by means of the EKG machine 5 relating to different cardiac phases. This means that all images of a slice recorded at different times are recorded during the same EKG phase; however, the individual slices are recorded in different EKG phases. Before the stress perfusion image record can be recorded, approximately 10 minutes must now pass before a contrast agent can again be applied. During this time, the first image record, that is to say a function data record, is recorded.

In the process, images are recorded in quick succession over an entire cardiac cycle, with it being possible to respectively record the EKG phase of each image using the EKG machine 5. These images are also stored on the computer 6. In addition, the patient 3 of course also holds his breath in the determined respiratory phase while the function image record is being recorded. After the contrast agent has been administered a second time, and medicines generating the corresponding stress have been administered, the stress perfusion image record is recorded using the same measurement protocol as for the rest perfusion image record. At this point it should be mentioned that it is also possible to later record a viability image record during the rest state after enriching the contrast agent in the necrotic tissue regions.

The first image record and the second image record or records are stored on the computer 6 after completing step S1. In this case, the image records are already registered to one another because they were recorded by the same imaging apparatus. In other cases it may be necessary to carry out a registration.

In step S2, the target volume 8 (in this case the myocardium) is segmented in the first image record, that is to say the function image record. This is particularly easy since the anatomical structures, in particular the boundaries of the myocardium, can easily be seen. FIG. 3, which should be viewed in conjunction with FIG. 2, schematically illustrates how the myocardium is segmented in the first image record 10, in which the boundaries 11 of the myocardium can easily be seen. This results in precise information 12 regarding the position and orientation of the myocardium. The function image record is segmented in at least each EKG phase in which one of the four slices of the perfusion image record, that is to say the second image record (reference symbol 13 in FIG. 3), was recorded. Should the function image record not contain an EKG phase exactly corresponding to the image data of the perfusion image record, a correction can be determined within the course of the method according to an embodiment of the invention.

The segmentation itself can be carried out in a number of ways. In the case of manual segmentation or semi-automatic segmentation, an image representation of the function image record is first of all displayed on the monitor 7. The user can make markings in it. For example, a starting point for region growing segmentation can be determined in the case of the semi-automatic method. However, automatic segmentation in which no user intervention is necessary is also conceivable and particularly advantageous. This segmentation can also use a region growing algorithm.

It should be noted that it is not necessary for segmentation to take place as late as the post-processing. It can also take place directly after recording the first image record 10, that is to say the function image record.

The precise position and orientation of the myocardium are known after segmentation. As illustrated in the second image record, referred to by 13 in FIG. 3 (in this case the perfusion image record), the boundary 11 of the myocardium is barely recognizable. Instead, locations 14 with a high contrast agent concentration are clearly visible. Due to the first image record 10 being registered to the second image record 13, it is now possible to use information 12 about both the position and orientation of the target volume 8 and also the registration in order to apply the target volume 8, segmented in the first image record 10, like a mask to the second image record 13—of course making sure that the EKG phases correspond—in order to select the region of the second image record 13 in which data about the target volume 8 is present. Thus, in step S3, the target volume image data (15 in FIG. 3) is selected from the second image record; it follows that only image data from the target volume 8 is contained in the target volume image data 15.

In step S4, the desired information is now determined from the target volume image data 15. In the case of perfusion diagnostics, the signal profiles in individual segments of the myocardium are usually the information of interest. To this end, an average value of the signal intensity in each individual segment is determined over time within these segments. (If required, the signal intensity can be corrected by subtracting the signal intensity prior to the contrast agent being administered.) Further information can be established from these signal intensity—time curves, such as the arrival time of the contrast agent in this segment, the maximum signal intensity attained, the wash-in time and the gradient of the increase. In the case of viability records, an average of the signal intensity per segment is also formed, from which, for example, the percentage of necrotic tissue or avital myocytes can be determined. In both cases described here, the information is thus established on a position-related basis.

Finally, the information is displayed in step S5. Possible displays are illustrated in FIGS. 4-6.

FIG. 4 shows a possible display of information relating to the perfusion in the myocardium in a perfusion image record, as displayed on the monitor 7. A graph which plots the signal intensity (SI) against time is illustrated. Three different curves I, II and III, which are associated with different segments of the myocardium, are illustrated in an example manner. Here, only three segments are represented as curves for reasons of clarity, although more segments are normally used, in particular seventeen segments. Whereas there is normal perfusion in segments I and II, less contrast agent is transported in and through segment III. A medical practitioner can draw appropriate diagnostic conclusions from this display.

A further display on the monitor 7 is illustrated in FIG. 5. Here, information regarding the signal intensity, and hence the perfusion, are superposed in a spatially precise manner on a first image representation of the first image record, the function image record, which shows the anatomy particularly well. The target volume 8 containing regions 16 of different signal intensity can be recognized clearly. This representation is possible because the information is established with respect to its location and the first and the second image record are registered to each other.

Finally, FIG. 6 shows a so-called bull's eye plot 17 on the monitor 7. Here, each section of the plot 17 represents a section of the myocardium. A color is now selected, based on the information present about the viability of each segment, in which the section of the plot 17 corresponding to the segment is shown; for example, white can be used for normal viability, cf. for example segments 18, blue for a certain amount of avital cells, cf. for example segment 19, and red can be used for mainly necrotic tissue, cf. for example segment 20. Of course, a display with different patterns or different grayscale values is also conceivable.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method for determining and displaying at least one item of information about a target volume, with the information being obtained from an image record, the method comprising:
    recording a first and at least one second image record of a target area including the target volume, the first image record having a relatively higher contrast than the at least one second image record with respect to boundaries of the target volume, and the first and the at least one second image record being registered to one another;
    segmenting the target volume in the first image record;
    selecting target volume image data in the at least one second image record, taking into account the segmentation and the registration;
    transferring the segmented target volume to the at least one second image record;

ensuring that a phase of the target volume in the first image record corresponds to a phase of the at least one second image record; and determining the information from the selected target volume image data, and displaying the information.

2. The method as claimed in claim 1, wherein the segmentation is carried out automatically, semi-automatically or manually.

3. The method as claimed in claim 1, wherein a region growing algorithm is used for the segmentation.

4. The method as claimed in claim 1, wherein the image records are recorded in a respiration-triggered fashion.

5. The method as claimed in claim 1, wherein the first image record is recorded over an entire EKG-cycle, with an EKG-phase being stored with every image, and wherein the at least one second image record is recorded in an EKG-triggered fashion and only images of the first image record with a same EKG phase are used for registration and segmentation.

6. The method as claimed in claim 1, wherein both the first and the at least one second image records are recorded in an EKG-triggered fashion during a same EKG-phase.

7. The method as claimed in claim 4, wherein, if there are no images of the first image record which correspond to the respiratory phase of images of the at least one second image record in the case of records of target areas rhythmically moving with the respiratory cycle, then a correction of at least one of the registration and the segmentation is determined based on a deviating phase.

8. The method as claimed in claim 1, wherein the first or the at least one second data record is recorded after a contrast agent is administered.

9. The method as claimed in claim 1, wherein the image records are recorded by a magnetic resonance scanner, with different recording sequences being respectively used for the two image records.

10. The method as claimed in claim 9, wherein the first image record is a function image record or a whole heart image record.

11. The method as claimed in claim 9, wherein the at least one second image record is a perfusion or viability record.

12. The method as claimed in claim 1, wherein the target volume is the myocardium.

13. The method as claimed in claim 1, wherein more than one second image record is recorded and wherein information from every second image record is recorded and displayed.

14. The method as claimed in claim 1, wherein additional information about the target volume is determined from the first image record and is displayed.

15. The method as claimed in claim 1, wherein an image representation of at least one of the first and the at least one second image record, and parts of at least one of the first and the at least one second image records is displayed.

16. The method as claimed in claim 1, wherein the information is established in a location-dependent manner and wherein the location-dependent information from imaging at least one of the first and the at least one second image record is displayed in a superposed fashion.

17. A medical examination apparatus, comprising:
   an imaging apparatus, in particular a magnetic resonance imaging scanner; and
   a computer device configured to:
      record a first and at least one second image record of a target area including a target volume, the first image record having a relatively higher contrast than the at least one second image record with respect to boundaries of the target volume, and the first and the at least one second image record being registered to one another;
      segment the target volume in the first image record;
      select target volume image data in the at least one second image record, taking into account the segmentation and the registration;
      transfer the segmented target volume to the at least one second image record;
      ensure that a phase of the target volume in the first image record corresponds to a phase of the at least one second image record; and
      determine the information from the selected target volume image data, and displaying the information.

18. The method as claimed in claim 2, wherein a region growing algorithm is used for the segmentation.

19. The method as claimed in claim 5, wherein, if there are no images of the first image record which correspond to the EKG phase of images of the at least one second image record in the case of records of target areas rhythmically moving with the EKG cycle, then a correction of at least one of the registration and the segmentation is determined based on a deviating phase.

20. The method as claimed in claim 10, wherein the at least one second image record is a perfusion or viability record.

21. The medical examination apparatus of claim 17, wherein the imaging apparatus is a magnetic resonance imaging scanner.

22. A non-transitory computer readable medium including program segments for, when executed on a computer device, causing the computer device to implement the method of claim 1.

* * * * *

UNITED STATES PATENT AND TRADEMARK OFFICE
CERTIFICATE OF CORRECTION

| | | |
|---|---|---|
| PATENT NO. | : 8,290,226 B2 | Page 1 of 1 |
| APPLICATION NO. | : 12/226858 | |
| DATED | : October 16, 2012 | |
| INVENTOR(S) | : Gühring et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 744 days.

Signed and Sealed this
Tenth Day of June, 2014

Michelle K. Lee
*Deputy Director of the United States Patent and Trademark Office*